United States Patent [19]

Crawley et al.

[11] 3,956,343

[45] May 11, 1976

[54] NOVEL 5-VINYL-3-ISOXAZOLYL SUBSTITUTED PYRIDINES

[75] Inventors: Lantz Stephen Crawley, Spring Valley, N.Y.; Sidney Robert Safir, River Edge, N.J.

[73] Assignee: American Cyanamid Company, Stamford, Conn.

[22] Filed: Apr. 4, 1975

[21] Appl. No.: 565,285

[52] U.S. Cl. ........................ 260/296 R; 260/307 H; 424/263
[51] Int. Cl.$^2$ ...................................... C07D 213/02
[58] Field of Search ..................... 260/296 R, 307 H

[56] References Cited
UNITED STATES PATENTS 3,598,829  8/1971  Bauer et al. ................. 260/294.8 D

OTHER PUBLICATIONS

Chemical Abstracts, Vol. 66, abst. no. 115636s, (1967), (abst. of Caramella).

Chemical Abstracts, Vol. 70, abst. 3903c, (1969), (abst. of Bertini et al.).

Chemical Abstracts, Vol. 77, abst. 62340j, (1972), (abst. of Iwakura et al.).

*Primary Examiner*—John D. Randolph
*Attorney, Agent, or Firm*—Edward A. Conroy, Jr.

[57] ABSTRACT

This disclosure describes 5-vinyl-3-isoxazolyl substituted pyridines and 5-vinyl-2-isoxazolin-3-yl substituted pyridines which possess anti-inflammatory activity.

9 Claims, No Drawings

NOVEL 5-VINYL-3-ISOXAZOLYL SUBSTITUTED PYRIDINES

BRIEF SUMMARY OF THE INVENTION

This invention relates to new organic compounds and, more particularly, is concerned with novel isoxazolyl and isoxazolinyl substituted pyridines which may be represented by the following general formula:

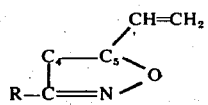

wherein R is α-pyridyl, β-pyridyl, or γ-pyridyl and the moiety $C_4-C_5$ is a trivalent radical of the formulae:

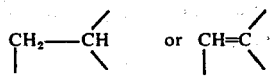

The novel compounds of the present invention form useful pharmaceutically acceptable acid-addition salts with a variety of non-toxic organic and inorganic salt-forming reagents. This, acid-addition salts, formed by admixture of the organic free base with one or two equivalents of an acid in a suitable solvent, are formed with such acids as acetic, butyric, ascorbic, citric, gluconic, maleic, lactic, tartaric, hydrochloric, hydrobromic, nitric, sulfuric, phosphoric, and the like. For purposes of this invention, the organic free bases are equivalent to their non-toxic acid-addition salts.

DETAILED DESCRIPTION OF THE INVENTION

The novel isoxazolyl substituted pyridines of the present invention may be readily prepared in accordance with the following reaction scheme:

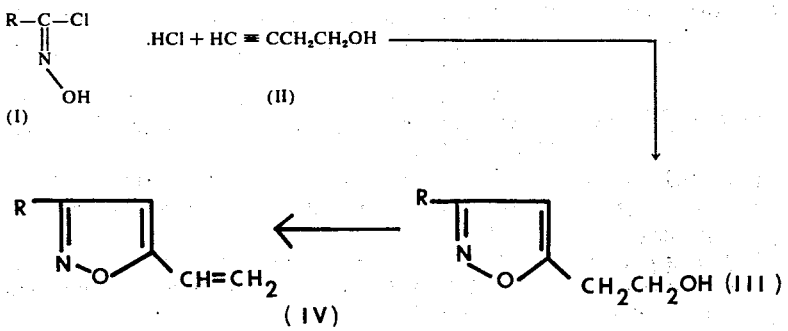

wherein R is as hereinabove defined. The acid chloride oxime hydrochloride (I) is reacted with 4-hydroxy-1-butyne (II) in the presence of a stoichiometric amount of triethylamine to provide the 5-isoxazoleethanol derivative (III). This reaction is preferably carried out in a solvent such as a lower alkanol at ambient temperature (15°–25°C.) for a period of time of about 1–2 hours. The 5-isoxazoleethanol intermediate (III) is readily converted to the 5-vinylisoxazole derivative (IV) by stirring in concentrated sulfuric acid at 0°–5°C. for a period of time of about ½ –1 hour. The novel isoxazolinyl substitutted pyridines of the present invention may be readily prepared by reacting the acid chloride oxime hydrochloride (I) with 1,3-butadiene in the presence of a stoichiometric amount of triethylamine under the same conditions as for the preparation of the intermediate (III).

The acute anti-inflammatory activity of the novel compounds of the present invention was determined by the following test procedure wherein Royal Hart, Wistar strain rats weighing 80–90 grams were used. The rats were fasted overnight prior to dosing but had free access to water. The drugs in aqueous solutions or suspensions were administered by gavage in a volume of 1.7 ml./5 g. of rat [corresponding to the hydration volume used by Winter, et al., Proc. Soc. Exp. Biol. & Med. 111, 544–547, (1962)]. The dosage of all compounds was 250 mg./kg. of body weight.

The phlogistic agent used was carrageenin prepared as a sterile 1% suspension in 0.9% sodium chloride for routine testing. A volume of 0.05 ml. was injected into the plantar tissue of the right hind paw. Measurements were made 5 hours after drug administration (4 hours after carrageenin challenge).

Volumes of both the normal and carrageenin inflamed feet as determined. The differences between the two measurements is considered to be the increased edema due to the carrageenin. Results are expressed as a Control (C)/Treated (T) efficacy ratio. (The ratio of mean edema volume of 8 control rats over the mean edema volume of 2 treated rats.) If the C/T ratio is equal to or greater than 1.41, the test is repreated. If the mean ratio of the two tests is equal to or greater than 1.43 the compound is considered active. Table I summarizes the results obtained with representative compounds of this invention.

TABLE I

| Compound | C/T Ratio |
| --- | --- |
| 3-(5-Vinyl-3-isoxazolyl)pyridine | 1.72 |
| 3-(5-Vinyl-2-isoxazolin-3-yl)-pyridine | 1.68 |
| 4-(5-Vinyl-2-isoxazolin-3-yl)-pyridine | 1.78 |

The active compounds of this invention can be used in oral compositions such as tablets or capsules wherein the active components are mixed with conventional fillers and binders such as corn starch, lactose, sucrose, sorbitol, talc, stearic acid, magnesium stearate, dicalcium phosphate or similar non-toxic, pharmaceutically acceptable ingredients. Liquid pharmaceutical dosage forms may be prepared wherein the compounds of this invention are incorporated for administration in suitably flavored emulsions with edible oils such as cottonseed oil, sesame oil, coconut oil, peanut oil, etc. as well as elixirs and similar pharmaceutical vehicles. Sterile suspensions or solutions can also be prepared for parenteral use.

The invention will be described in greater detail in conjunction with the following specific examples.

EXAMPLE 1

Preparation of 3-(3-pyridyl)-5-isoxazoleethanol

To a stirred suspension of 19.3 g. of nicotinoyl chloride oxime hydrochloride and 35 g. of 4-hydroxy-1-butyne in 500 ml. of absolute ethanol was added dropwise, over a one hour period, a solution of 22.2 g. of triethylamine in 200 ml. of ethanol. The reaction was stirred at room temperature for one hour and the solvent removed by evaporation. The dry residue was mixed with diethyl ether and filtered. The filtrate was concentrated to produce a light yellow solid which was collected by filtration and recrystallized from diethyl ether, m.p. 80°–82°C.

By substituting an equimolar amount of picolinoyl chloride oxime hydrochloride or isonicotinoyl chloride oxime hydrochloride for the nicotinoyl chloride oxime hydrochloride employed in the above example, there is obtained the corresponding 3-(2-pyridyl)-5-isozazoleethanol and 3-(4-pyridyl)-5-isoxazoleethanol.

EXAMPLE 2

Preparation of 3-(5-vinyl-3-isoxazolyl)pyridine

Five ml. of concentrated sulfuric acid was cooled to 0°C. in an ice bath and added directly to 0.5 g. of 3-(3-pyridyl)-5-isoxazoleethanol. The reaction was allowed to stir ½ hour at 0°C. and then was poured over 50 g. of ice. The resulting solution was made basic with 5N NaOH, and was extracted with CHCl$_3$. The organic layer was dried over sodium sulfate. Removal of the solvent resulted in a white oil which crystallized on standing, m.p. 60°–64°C.

By substituting an equimolar amount of 3-(2-pyridyl)-5-isoxazoleethanol or 3-(4-pyridyl)-4-isoxazoleethanol for the 3-(3-pyridyl)-5-isoxazoleethanol employed in the above example, there is obtained the corresponding 2-(5-vinyl-3-isoxazolyl)-pyridine and 4-(5-vinyl-3-isozazolyl)pyridine.

EXAMPLE 3

Preparation of 3-(5-vinyl-2-isoxazolin-3-yl)pyridine hydrochloride

To a stirred suspension of 27.0 g. of nicotinoyl chloride oxime hydrochloride and 30.2 g. of 1,3-butadiene in 500 ml. of absolute ethanol was added dropwise, over a one hour period, a solution of 29.3 g. of triethylamine in 200 ml. of ethanol. The reaction was stirred at room temperature for one hour, the solvent was removed by evaporation and the residue mixed with water and filtered. The solid was dissolved in diethyl ether and washed several times with water. The ether layer was separated, dried over sodium sulfate and filtered to remove solids (drying agent). Removal of the solvent left a red orange liquid which was dissolved in diethyl ether and HCl gas was bubbled in to form a white solid which was collected by filtration and recrystallized from ethanol. Recrystallization was repeated a second time. The hydrochloride salt melts at 201°–204°C.

EXAMPLE 4

Preparation of 4-(5-vinyl-2-isoxazolin-3-yl)pyridine

To a stirred suspension of 3.96 g. of isonicotinoyl chloride oxime hydrochloride and 7.0 g. of 1,3-butadiene in 100 ml. of absolute ethanol was added dropwise, over a one hour period, a solution of 4.11 g. of triethylamine in 40 ml. of ethanol. The reaction was stirred at room temperature for one hour and the solvent removed by evaporation. The resulting solid was mixed with diethyl ether and filtered. The filtrate was evaporated to dryness and the residue dissolved in chloroform, dried over sodium sulfate and filtered to remove solids (drying agent). Evaporation of the solvent from the dried filtrate resulted in a tan solid. Double recrystallization from diethyl ether provided a solid which melts at 91°–93.5°C.

By substituting an equimolar amount of picolinoyl chloride oxime hydrochloride for the isonicotinoyl chloride oxime hydrochloride employed in the above example, there is obtained the corresponding 2-(5-vinyl-2-isoxazolin-3-yl)pyridine.

We claim:

1. A compound selected from the group consisting of those of the formulae:

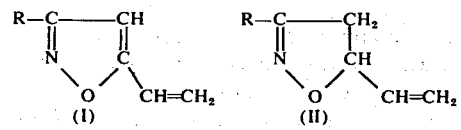

wherein R is α-pyridyl, β-pyridyl, or γ-pyridyl; and the pharmacologically acceptable acid-addition salts thereof.

2. The compound according to claim 1, formula (I), wherein R is α-pyridyl; 2-(5-vinyl-3-isoxazolyl)pyridine.

3. The compound according to claim 1, formula (I), wherein R is β-pyridyl; 3-(5-vinyl-3-isoxazolyl)pyridine.

4. The compound according to claim 1, formula (I), wherein R is γ-pyridyl; 4-(5-vinyl-3-isoxazolyl)pyridine.

5. The compound according to claim 1, formula (II), wherein R is α-pyridyl; 2-(5-vinyl-2-isoxazolin-3-yl)pyridine.

6. The compound according to claim 1, formula (II), wherein R is β-pyridyl; 3-(5-vinyl-2-isoxazolin-3-yl)pyridine.

7. The compound according to claim 1, formula (II), wherein R is γ-pyridyl; 4-(5-vinyl-2isoxazolin-3-yl)pyridine.

8. The process of preparing compounds of formula (I) of claim 1 which comprises reacting a compound of the formula:

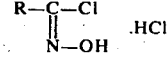

wherein R is α-pyridyl, β-pyridyl, or γ-pyridyl with 4-hydroxy-1-butyne in the presence of triethylamine in an inert solvent at ambient temperature for about 1–2 hours.

9. The process of preapring compounds of formula (II) of claim 1 which comprises reacting a compound of the formula:

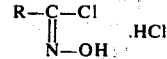

wherein R is α-pyridyl, β-pyridyl, or γ-pyridyl with 1,3-butadiene in the presence of triethylamine in an inert solvent at ambient temperature for about 1–2 hours.

* * * * *